United States Patent [19]

Sibalis

[11] Patent Number: 4,883,457

[45] Date of Patent: Nov. 28, 1989

[54] DISPOSABLE AND/OR REPLENISHABLE TRANSDERMAL DRUG APPLICATORS AND METHODS OF MANUFACTURING SAME

[75] Inventor: Dan Sibalis, Stony Brook, N.Y.

[73] Assignee: Drug Delivery Systems Inc., New York, N.Y.

[21] Appl. No.: 58,527

[22] Filed: Jun. 5, 1987

Related U.S. Application Data

[63] Continuation-in-part of Ser. No. 807,234, Dec. 10, 1985, Pat. No. 4,731,926, Continuation-in-part of Ser. No. 702,486, Feb. 19, 1985, abandoned, Continuation-in-part of Ser. No. 660,192, Oct. 12, 1984, Pat. No. 4,622,031, Continuation-in-part of Ser. No. 524,252, Aug. 18, 1983, Pat. No. 4,557,723.

[30] Foreign Application Priority Data

| Nov. 18, 1986 | [TW] | Taiwan | 75105482 |
| Nov. 20, 1986 | [AR] | Argentina | 305963 |
| Nov. 28, 1986 | [EP] | European Pat. Off. | 86116547.0 |
| Nov. 28, 1986 | [KR] | Rep. of Korea | 10126/86[U] |
| Dec. 3, 1986 | [AU] | Australia | 66193/86 |
| Dec. 5, 1986 | [CO] | Colombia | 263611 |
| Dec. 9, 1986 | [BR] | Brazil | PI8606062[U] |
| Dec. 9, 1986 | [CA] | Canada | 524873 |
| Dec. 9, 1986 | [JP] | Japan | 61-293319 |
| Dec. 9, 1986 | [MX] | Mexico | 4602 |
| Dec. 10, 1986 | [VE] | Venezuela | 2160/86 |

[51] Int. Cl.$^4$ .................................... A61N 1/30
[52] U.S. Cl. .................................... 604/20; 128/798
[58] Field of Search ................. 128/798, 802, 803; 604/20

[56] References Cited

U.S. PATENT DOCUMENTS

| 385,567 | 7/1988 | Hoke | 403/68 |
| 486,902 | 11/1892 | Shultz | 604/20 |
| 588,479 | 8/1897 | Roedel | 604/20 |
| 2,493,155 | 1/1950 | McMillan | 604/20 |
| 2,667,162 | 1/1954 | Zwahlen | 604/20 |
| 2,784,715 | 3/1957 | Kestler | 604/20 |
| 3,163,166 | 12/1964 | Brandt et al. | 604/20 |
| 3,289,671 | 12/1966 | Troutman et al. | 604/20 |
| 3,547,107 | 12/1970 | Chapman et al. | 604/20 |
| 4,008,721 | 2/1977 | Burton | 128/802 |
| 4,141,359 | 2/1979 | Jacobsen et al. | 604/20 |
| 4,239,046 | 12/1980 | Ong | 128/798 |
| 4,243,052 | 1/1981 | Bailey | 128/798 |
| 4,250,878 | 2/1981 | Jacobsen et al. | 604/20 |
| 4,273,135 | 6/1981 | Larimore et al. | 128/802 |
| 4,292,968 | 10/1981 | Ellis | 604/20 |
| 4,314,554 | 2/1982 | Greatbatch | 604/20 |
| 4,325,367 | 4/1982 | Tapper | 128/803 |
| 4,367,745 | 1/1983 | Welage | 128/303.13 |
| 4,406,658 | 9/1983 | Lattin et al. | 604/20 |
| 4,419,091 | 12/1983 | Behl et al. | 604/20 |
| 4,474,570 | 10/1984 | Ariura et al. | 604/20 |

FOREIGN PATENT DOCUMENTS

| 2263792 | 10/1975 | France . | |
| 694198 | 10/1979 | U.S.S.R. . | |
| 8102097 | 8/1982 | World Int. Prop. O. | 128/640 |

Primary Examiner—Max Hindenburg
Assistant Examiner—Randy Citrin
Attorney, Agent, or Firm—Lackenbach, Siegel, Marzullo & Aronson

[57] ABSTRACT

Applicators for the electrophoretic and/or electroosmostic dispensing of a medicament across the skin and into the bloodstream of a patient. Each applicator includes two electrodes in electrical contact with the skin with at least one of the electrodes being a drug reservoir, at least one battery, a flexible, non-conductive substrate having an electrically conductive coating extending to electrical contact with each electrode and to the terminals of the battery, the substrate being folded into at least two layers, a cover adhesively secured to the applicator, and a release liner covering and protecting the drug reservoir or reservoirs until use.

27 Claims, 9 Drawing Sheets

FIG. 4
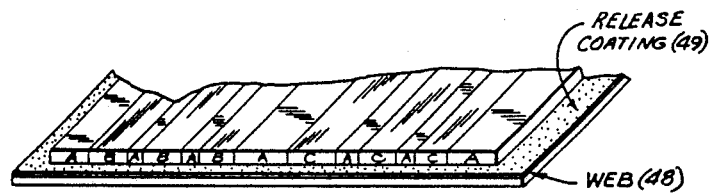
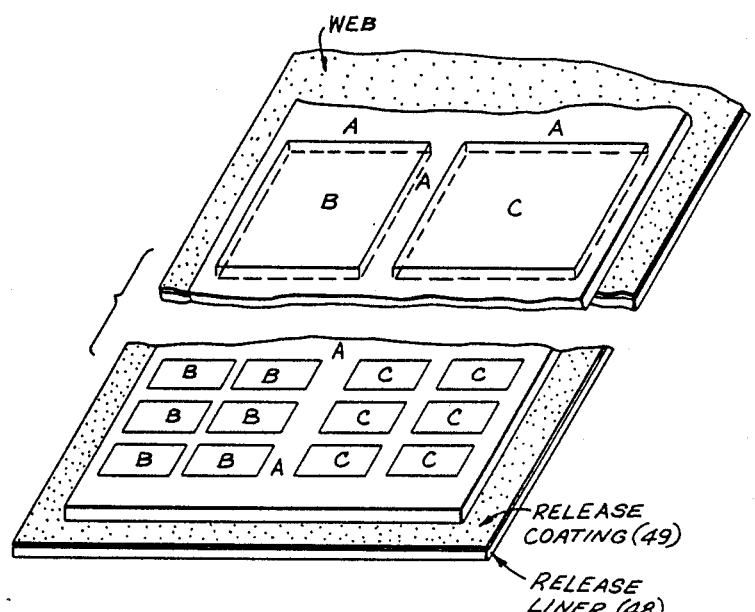
FIG. 5

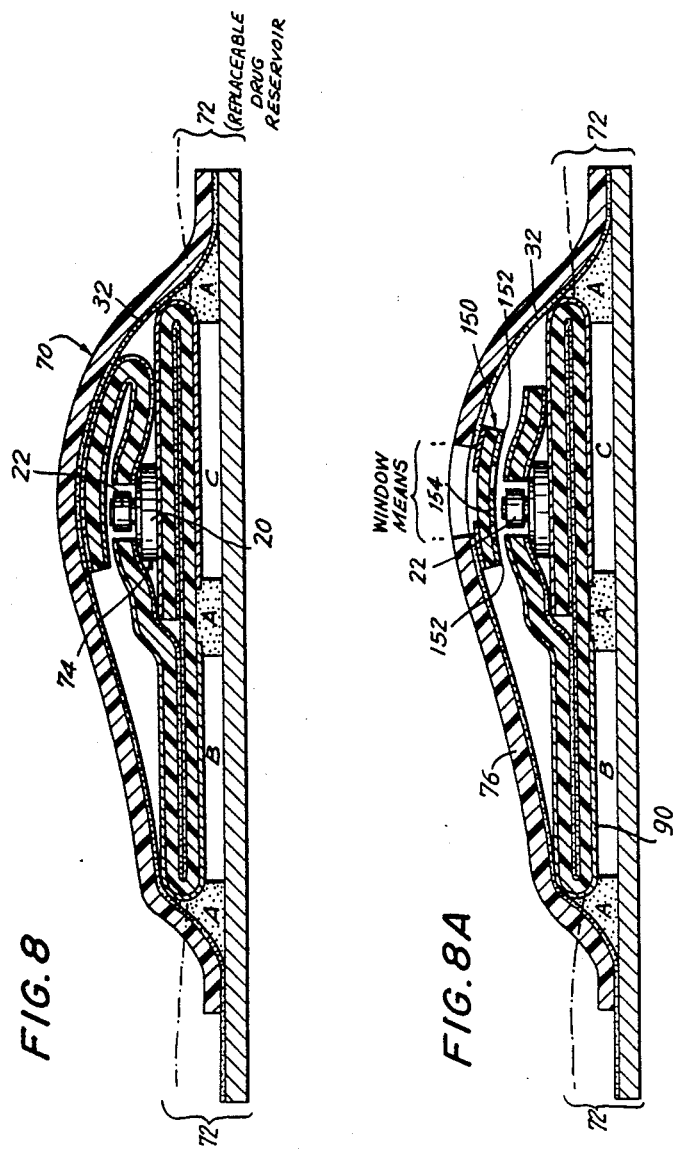

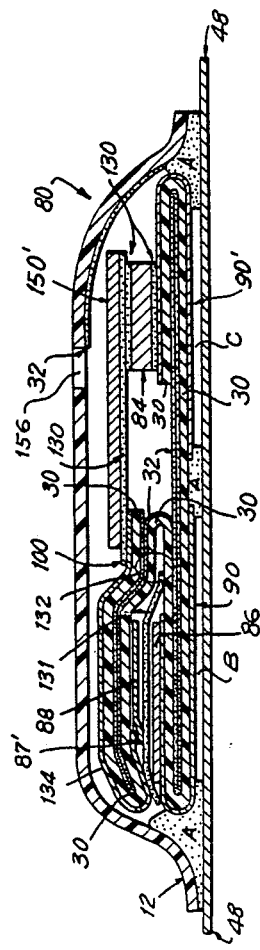
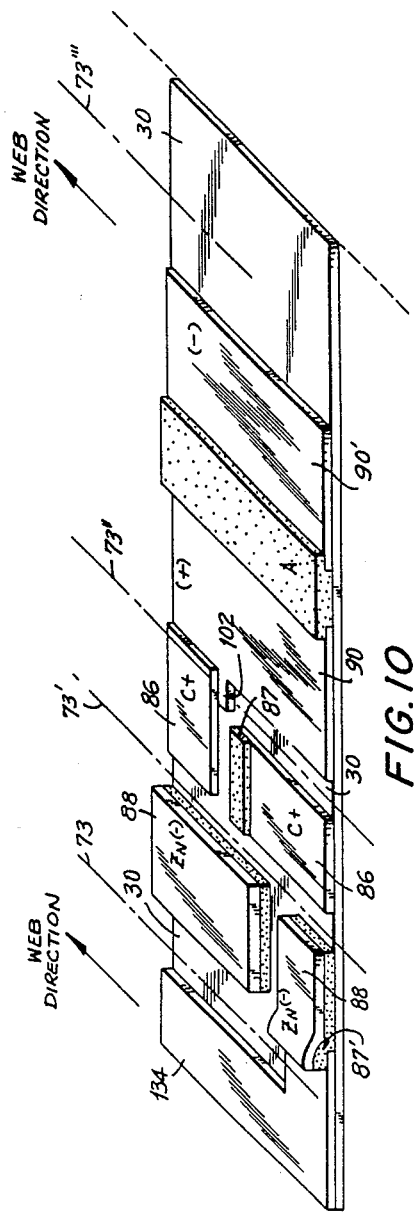

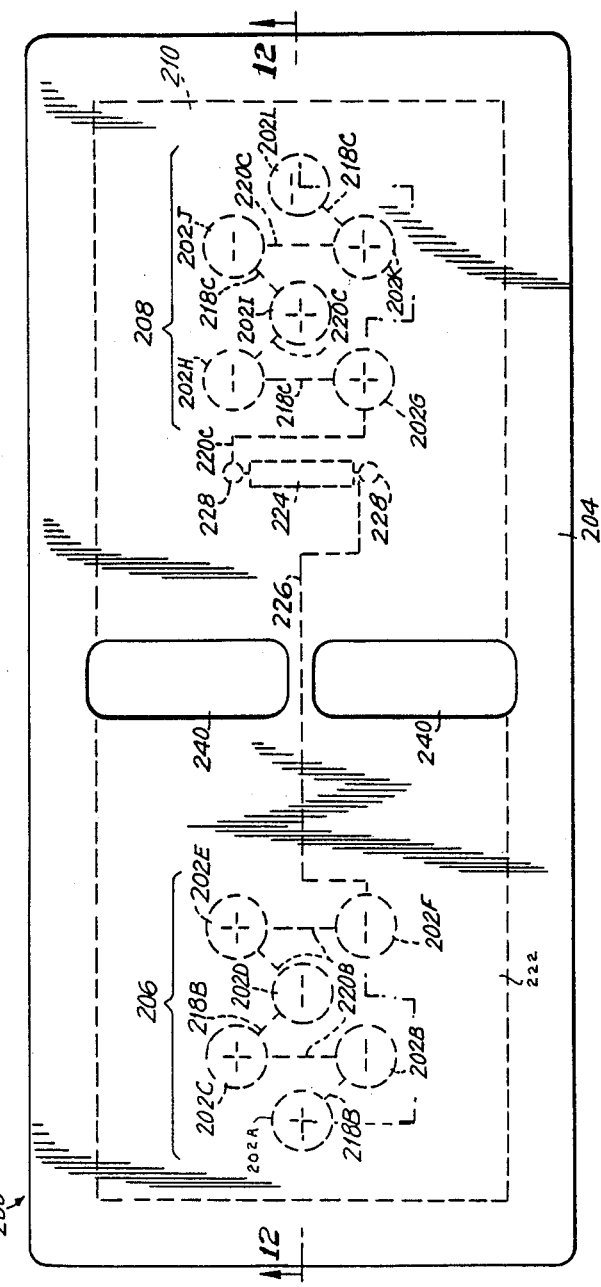

DISPOSABLE AND/OR REPLENISHABLE TRANSDERMAL DRUG APPLICATORS AND METHODS OF MANUFACTURING SAME

RELATED U.S. PATENT APPLICATIONS

This application is a continuation-in-part of U.S. patent application, Ser. No. 807,234; filed Dec. 10, 1985, now U.S. Pat. No. 4,731,926, which is a continuation-in-part of Ser. No. 702,486, filed Feb. 19, 1985, now abandoned which in turn is a continuation-in-part of earlier filed patent applications; Ser. No. 660,192, now U.S. Pat. No. 4,622,031, filed Oct. 12, 1984; and Ser. No. 524,252, now U.S. Pat. No. 4,557,723, filed Aug. 18, 1983; all of the above-identified patent applications, as well as the instant patent application currently assigned to Drug Delivery Systems Inc.

INCORPORATION BY REFERENCE

This application incorporates by reference my earlier filings, Serial No. PCT/US85/01075, filed June 10, 1985; and Ser. No. 702,486, filed Feb. 19, 1985, complete copies of which are attached hereto and expressly made a part of this disclosure as pages A1 through A-76 as a matter of convenience.

Field of the Invention

This invention relates to disposable as well as replenishable transermal drug applicators which are electrically powered, and to methods for making such constructions. A complete electrical circuit is made through the skin once the drug applicator is adhered thereto, whereby at least one physico/chemical mass transfer phenomenon takes place causing the drug or medicament to migrate through the skin.

BACKGROUND OF THE INVENTION

Reference to or disclosure of devices for transdermal delivery of drugs by application of electrical current through the skin of a person or animal are shown in the following U.S. patents:

| | |
|---|---|
| 385,556 | 4,243,052 |
| 486,902 | 4,325,367 |
| 588,479 | 4,367,745 |
| 2,493,155 | 4,419,091 |
| 2,267,162 | 4,474,570 |
| 2,784,715 | 4,406,658 |
| 3,163,166 | 4,314,554 |
| 3,289,671 | 4,166,457 |
| 3,547,107 | 4,239,052 |
| 3,677,268 | 4,250,878 |
| 4,008,721 | 4,164,226 |
| 4,141,359 | 4,362,645 |
| 4,239,046 | 4,273,135 |

The following foreign patents refer to or disclose transdermal delivery devices:
EPA 0060452
DE 290202183
DE 3225748
EPA 0058920
UK 2104388

BRIEF DESCRIPTION OF THE DRAWINGS

FIGS. 4 and 5 are fragmentary perspective views of typical configurations of drug electrodes/reservoirs provided on endless web substrates fed from rolled stock material, with occlusive adhesive dams separating the drug reservoirs longitudinally, as well as transversely;

FIG. 8 is a cross-sectional view of a disposable drug applicator with a separate subassemblied power source and electrical conditioning means adhesively assembled along their electrodes to any one typical drug electrode/reservoir assemblies shown in FIGS. 6–7;

FIG. 8A is a cross-sectional view similar to that shown in FIG. 8, but illustrating an alternate drug applicator construction in which the outer conformal cover has window means through which current induced color changes or other visual feedback information can be viewed for verification of status of the drug delivery system, such as drug delivery taking place or having been terminated.

FIG. 9 is a cross-sectional view of an alternate construction having similarly optionally replaceable drug reservoirs (electrodes/reservoirs), and with flat batteries forming a sub-assembly with electrical connections to electronic conditioning means;

FIG. 10 illustrates an endless such substrate fed from rolled stock material upon which is provided thin sheet electrodes for the flat batteries and other rolled, layered materials for forming the power-source sub-assembly shown in FIG. 9;

FIG. 11 illustrates a top view embodiment of the drug applicator having the end portions of the substrate folded downwardly and having a number of bottom batteries;

DESCRIPTION OF THE PREFERRED EMBODIMENTS

It should also be noted that as a convenience in the following description of the invention, like numerals are representative of similar elements common to the various embodiments of the invention.

Figure 1:
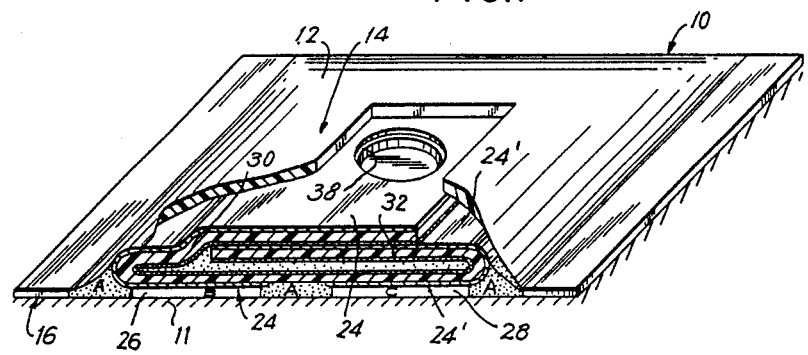
FIG. 1 is a perspective view, paertially cut away, so as to illustrate the innards of a selfcontained drug applicator of the invention.
Figure 2:
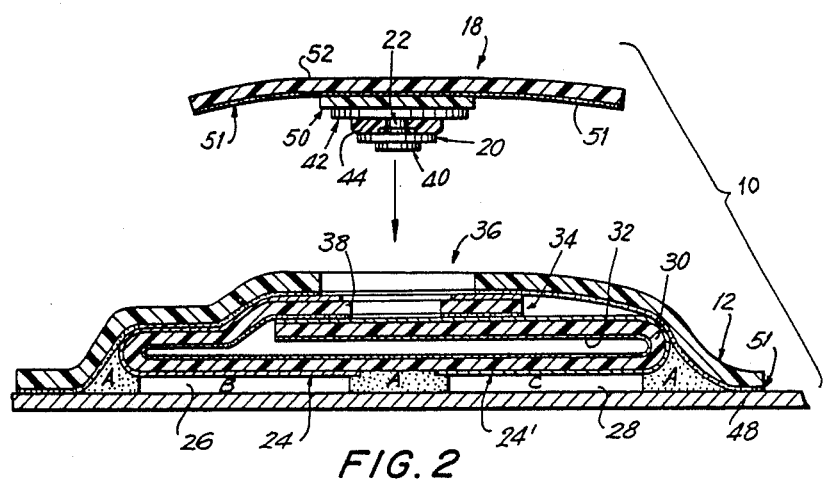
FIG. 2 is a longitudinal cross-sectional view of the drug applicator of FIG. 1, and also illustrating in exploded view a reusable power supply which may be provided with a programmable control and wrist watch mounting.

Referring now to FIGS. 1–2, there is shown a transdermal drug applicator 10 which is adhered to the skin 11 comprising an outer cover 12 with a centrally raised portion 14 and a peripheral sealed area or lip portion 16. Such an applicator is of the replaceable type having provision for connection to a reusable power supply 18 which may be, if desired, part of a wrist watch mounting having optionally a programmable control device such as more particularly described and claimed in said aforementioned earlier filed patent application, Ser. No. PCT/US85/01075, filed June 10, 1985.

Power supply 18 comprises a suitable disc battery 20 having electrodes or terminals on opposite sides thereof one battery electrode is electrically connected to current conditioning or electronic conditioning means 22 and by means of suitable snap-on or other type of mechanical connectors (silver-plated Velcro connections manufactured by Velcro Corporation of America) or by conductive and reusable adhesives; and the battery electrodes are in turn connected to conductors 24, 24' extending from drug reservoirs 26, 28, which are also indicated as reservoirs B and C, respectively. The conductors 24, 24' are flexible, suitably conductive surfaces or coatings on a flexible plastic substrate 30 which is non-conductive, impermeable, stable and otherwise compatible with drugs, adhesives, the skin and any other materials from which the device is fabricated. Each conductor 24, 24' with its substrate 30 forms a seamless, onepiece, folded member. When bent and folded back upon itself the plastic substrate 30 and conductive surfaces bring the electrical contacts 24, 24' to the top side of the drug applicator where the electrical connections are to be made with the reusable power supply 18. The adhesive coating 32 on the inside (and topside) of the plastic substrate 30 secures together the mating surfaces as well as the overlapping edge or end 34 which is provided with a suitable slot or aperture 36 representing a nest or well area for receiving the power supply 18 and its electrical connectors. A small peripheral clearing 38 about the aperture 36 represents an insulating guard area to preclude any possibility of shorting out. Thus, the lower electrode 40 and upper electrode 42 of the battery directly or indirectly make electrical contact with conductors 24, 24'. Suitable insulating material 44 surrounds the current or electronic conditioning means 22 and suitable insulating material "A", which forms the dam separating the drug reservoirs 26, 28 and provides the end seals for not only the side of longitudinal edges but also for the transverse edges of the transdermal drug applicator. Conformable cover 12 protects the entire device and may be suitably of a skin tone or color and the like appearance.

Should snaps or other type of material fasteners be employed, it is preferable if the disposition of same is such that the snaps are not symmetrically laid out as such arrangement would ensure that the power supply could only be mated in a single manner.

With the drug applicator shown being of electrode/reservoir constructions of the side by side type, the cover need not be conductive as the lip portion merely acts as a peripheral seal and not a return electrode. However, it will be appreciated that the invention is also applicable to drug applicators of the "matted" frame construction where the lip portion acts as the return or inactive electrode. In such case, then the conformable cover must also be conductive. Electrokinetic mass transfer processes require an electric power source, and in the case of electrophoresis an ionized drug migrates from the drug applicator patch through the skin and into the blood stream, whereas in the case of electroosmosis, a fluid carrier, such as water is likewise transported across the skin and into the blood stream carrying along with it any and all dissolved constituents (ionized drugs or otherwise). Either or both of these two physiochemical phenomena may jointly work together or independently in transdermally carrying a drug or drugs across the skin in a desired dosage release and/or relatively steady pattern.

The application of an electric field across the skin greatly enhances the skin permeability to various drugs.

Prior to the attachment to the skin, a suitable release liner or web, 48 is removed leaving the two drug reservoirs, insulating dam and peripheral seals free to adhere to the skin.

It should also be understood that the power supply 18 is supported by a like plastic substrate 50 which is in turn suitably adhesively secured by adhesive 51 to a small conformal cover 52 which neatly covers over and seals off the apertured area where the electrical connections are made. This ensures that the device can be worn at all times; such as in the rain or in the shower or bath.

Figure 2A:
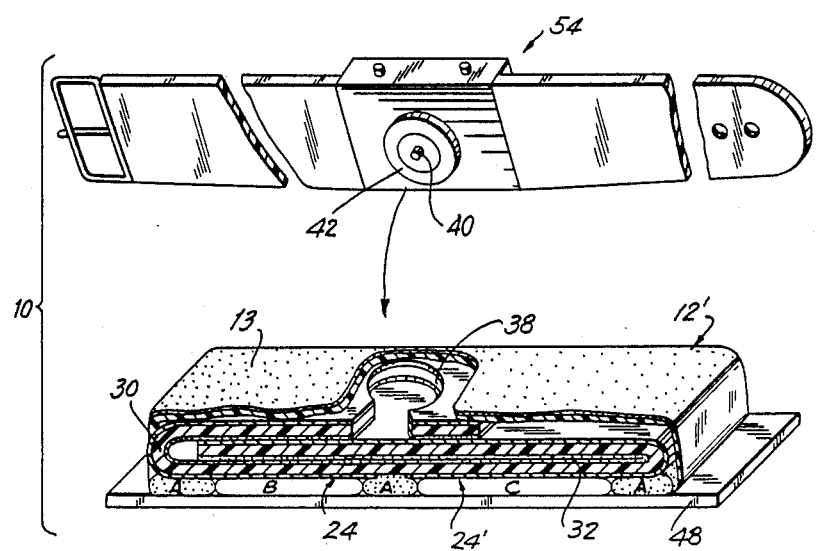
FIG. 2A is a view similar to FIG. 2, but shown perspectively, in which the power supply and the programmable control are contained within a wrist watch mounting having concentric connectors.

If desired, the reusable power supply 18 may be part of a wrist watch 54, as shown in FIG. 2A, having a programmable computer with concentric conductive adhesive connectors 40, 42, such as previously disclosed in said earlier patent filing with like electrical connections and mechanical securement being provided where needed to achieve such packaged construction. The main difference between the disposable drug applicators shown in FIGS. 2 and 2A is that the conformal cover means 12' of FIG. 2A is coated with an adhesive layer 13. Such adhesive layer 13 allows removal of the drug applicator and replacement same as adhesive 51 in FIG. 2.

Figure 3:
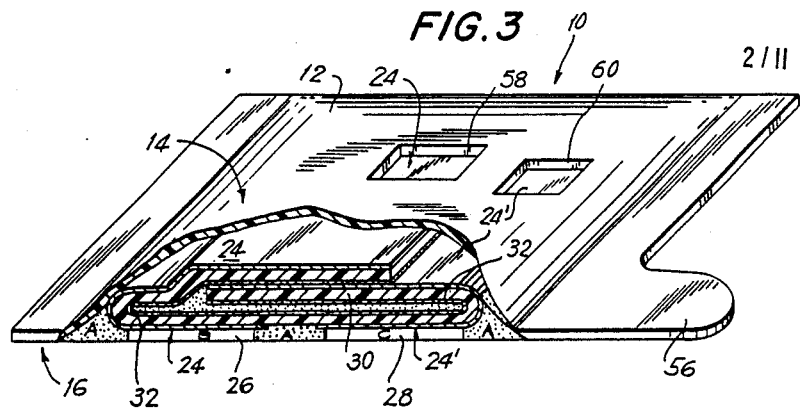
FIG. 3 is another perspective view similar to FIG. 1, but showing an alternate construction having a pair of off-center apertures or slots for the electrical contacts made through the use of a single center aperture so as to enable the mounting of a new drug applicator to the reusable power supply in a keyed or polarized manner.

The alternate construction shown in FIG. 3 simply adds the feature of an optimal tab 56 for the release liner or paper 48, and the use of offset apertures 58 and 60 for mating with the conductive adhesive contacts at the bottom of battery 20 and the extended substrate 50 which may be offset in a manner to provide just side to side connection in lieu of concentric or symetric connections.

In FIGS. 4–7, drug sub-assemblies are illustrated for use with the disposable transdermal drug applicators shown in FIGS. 8–9. As shown in FIGS. 4 and 5, the drug reservoirs may be suitable gel layers which can be rolled or otherwise applied to webbed substrate 48, discussed previously, fed from endless rolled sheet material while being separated between reservoirs and about their extreme edges by applied occlusive adhesive dams. The dams are identified by the Letters A and the drug reservoirs are marked with the Letters B representing negative and C representing positive The "quilt" type pattern where multiple drug reservoirs are employed can be fabricated by repetitive operative steps using a silk screen printing or transfer process. It should also be recognized that the substrate is coated with a suitable release agent 49, such as silicone and when the sub-assembly is combined into a complete transdermal drug applicator or patch, the substrate in effect becomes the release liner 48, discussed previously.

Figure 6:
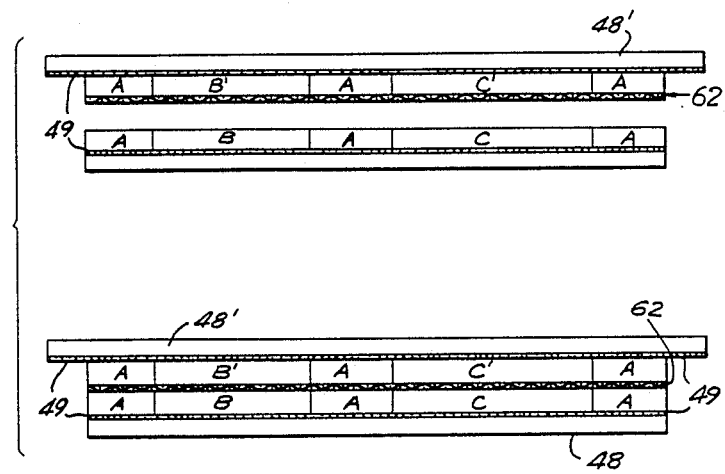
FIGS. 6 and 7 respectively illustrate diagrammatically typical assemblies of drug electrodes/reservoirs forming larger reservoir means; or forming drug gradient with layers of both high and low drug concentration within reservoirs separated by a semipermeable membrane or reinforcing scrim.
Figure 7:
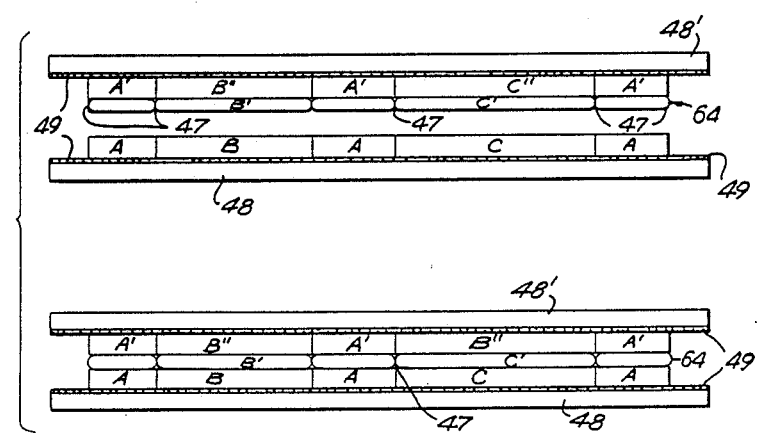

FIGS. 6-7 illustrate the assembly of two drug applicator sub-assemblies. For example, in FIG. 6 an optional reinforcing web or vail-like material (scrim) 62 may be used to reinforce the gel "drug" reservoirs.

One embodiment uses an open cell foam which is impregnated in different areas with gel drug reservoirs surrounded by occlusive adhesive dam penetrating the same open cell foam. Such a structure allows the construction of a thick replaceable drug reservoir in which the gel will maintain its integrity during manufacturing, the application to and removal from human skin, as well as to the replacement of exhausted drug reservoirs. In manufacture, the open cell foam web may be suitably attached to a release liner, then provided with occlusive adhesive dams which completely penetrate the full thickness of the open cell foam, thus forming or designating the drug reservoir areas which can be subsequently filled in with their respective drug/gel mixtures.

As one 48' of the two disposed release liners can be further discarded in production, it can be considered optional, bearing in mind that the gel reservoirs and dams are viscous and retain their shape, and may even be further supported by a reinforcing web 62. FIG. 7 simply differs in that a semi-permeable membrane 64 is provided between the two sub-assemblies so that upon assembly, drug reservoirs are formed with areas or zones of different drug concentration or composition. Such a type of drug reservoir is noted to have significant advantages during operation of the transdermal device. Note that appropriate seals 47 can be provided along the semi-permeable membranes at the edges where each reservoir ends by means of heat or by other means to collapse the voids and seal the semipermeable membrane in those areas 47 where the seals are necessary. Alternately, silicone dams could also be used as seals between zones of semi-permeable materials. In addition, the semi-permeable materials may be preimpregnated with drugs or other chemicals which might be employed. These sub-assemblies of FIGS. 4–7 will now be shown and described as assembled onto the sub-assembly of FIG. 10. For purposes of disposability of the drug reservoirs, these sub-assemblies (FIGS. 4–7) are disposable and like replacements may be used to replenish the drug supply.

The disposable drug applicator 70 shown in FIG. 8 comprises an optionally replaceable drug reservoir sub-assembly 72 (any one of FIGS. 4–7) and a further sub-assembly 74 for the power means and electrical conditining means which assemblies are secured together by suitable conductive adhesives. Sub-assembly 74 comprised essentially of battery 20 and current conditioning means 22 and associated reservoir conductors 24, 24' as best shown in FIG. 2. The elctrical circuit running between the drug reservoirs and through the skin is a loop similar to that of FIG. 2, the only difference being the permanent nature of the battery and current/electrical conditioning means in the applicator structure rather than the reusable nature of the FIG. 2 embodiment. However, here just the drug reservoir sub-assembly 72 may be replaced where required.

In FIG. 8A, the cover means 76 is suitably provided with window means, as is shown, which allows the status of the drug applicator to be observed. Such indicator means which is observed through the window means is more particularly described in my earlier filed U.S. patent application, Ser. No. 660,192, filed Oct. 12, 1984. As shown in FIG. 8A, the indicator means 150 is electrically in series with the current conditioning means 22 and conductive surface 90 which powers drug reservoir B. The connections of said indicator means 150 to the current conditioning means 90 and the conductive surface are achieved by means of a suitable flexible conductive adhesive, as is shown at the contact joints 152 and 154.

FIG. 9 represents a like kind of disposable drug applicator 80 having an optionally replaceable drug reservoir sub-assembly 72 as illustrated in FIGS. 8–8A, and a power source or flat layered battery, as well as electrical or current conditioning means 84 sub-assembly which are secured together by suitable conductive adhesives. In this modification, the battery embodies sheet elecrodes such as carbon (+) reference number 86 and zinc(−), reference number 88 and the drug reservoir electrodes 90, 90' which also are thin and flat. The battery electrodes 86, 88 are adhesively connected to a plastic substrate 30. The webbed material in production is preferably folded along the illustrated longitudinal fold lines, 73,73',73'',73''' (and others may be required depending upon the required number of folds) cut transversely to a predetermined size. One carbon electrode 86 which is connected to the drug reservoir electrode 90 forms a battery with the large zinc electrode 88. The carbon electrode 86 which is connected to electrode 90 could be made as one unitary element. This large zinc electrode 88 is electrically connected to the other carbon electrode 86 by means of the conductive adhesive strip 87 (FIG. 10) at one end thereof, and thus forms a second battery, in series with the first battery, in conjunction with the small zinc electrode 88 which is likewise electrically connected to conductive surface 134 at 87' or simply with a conductive adhesive strip similar to 87.

It will be apparent to those skilled in the art that most or all of the battery components and connections within the applicator constructions of the invention could be applied by silk screen or rotogravure printing or, printed, die cut and stripped at high speed on standard roll label equipment.

A suitable current or other electronic conditioning means 84 is secured by a conductive adhesive 130 to one of the drug electrode conductive surfaces 90' having a flexible plastic substrate 30 and is also electrically connected to one of the battery electrodes, shown at 100 by means of an optional conductive indicator 150'. Optionally, a window means, such as a transparent area 156 of the cover 12 or an opening in said cover allows the viewing of an optional indicator 150'. In such case, the indicator 150' replaces the conductive connector. The last battery electrode, shown at 88 is electrically connected to the other drug electrode conductive surface 90 to form a complete electrical loop between the two drug reservoirs and through the skin. A suitable battery electrode element 131 impregnated with a gelled battery electrolyte is inserted between the carbon and zinc electrodes prior to folding, and the peripheries of the battery compartments are suitably sealed at 132 to prevent electrolyte leakage. In this modification, the drug reservoirs are also optionally removable if desired, as was shown in FIGS. 8–8A. It should also be apparent that in this modification, some adhesives employed may also be conductive while in other instances it is inherent that the adhesive has no other function than to secure together objects so it need not necessarily be conductive and in some cases it must not be conductive or a short circuit would occur. Also, the voltage of the battery will determine the numbers of carbon and zinc electrodes required, and such voltage can vary depending upon the applications. Although only carbon/zinc batteries are illustrated, other type battery cells could be made in a similar manner.

It will be apparent to those skilled in the art that various combinations of the previously described stages of applicator constructions can be embodied within one drug applicator device. For example, the function of the substrate 48' of FIGS. 6 or 7 could be provided by the electrode area 90, 90' of FIG. 10 in which case the addition of the second drug reservoir with its substrate (release liner 48) completes the product. It should also be evident that the construction shown in FIGS. 6 and 7 describes the replaceable drug reservoir which is employed by the end user (patient, nurse or doctor) by peeling off the release liner 48, applying the drug reservoir to the area 90, 90' of power supply applicator construction which results in the device shown in FIG. 9 which then could be applied on the human skin after peeling off the release liner 48. In this particular construction, it is envisioned that the battery life will be sufficient for the use of the applicator of FIG. 9 with a predetermined number of "refills" (similar to FIGS. 6 or 7) when marketed together in kit form. The same would hold true for all the other alternate constructions and embodiments of the invention. The power supply and the current regulating or electronic conditioning means is designed to peform only for a predetermined number of "refills" so as to guarantee medical supervision for each set of treatments (kit).

A current limiting resistor, in series with the battery can be manufactured by controlling the resistance of the conductive surfaces. Thus, such use would make the device fail safe and could provide current regulation in addition to or instead of solid state conditioning means 22 of FIG. 8. Therefore, if the current conditioning means 22 of FIG. 8 short circuits this resistor will limit the current to safe value or level.

Figure 12:
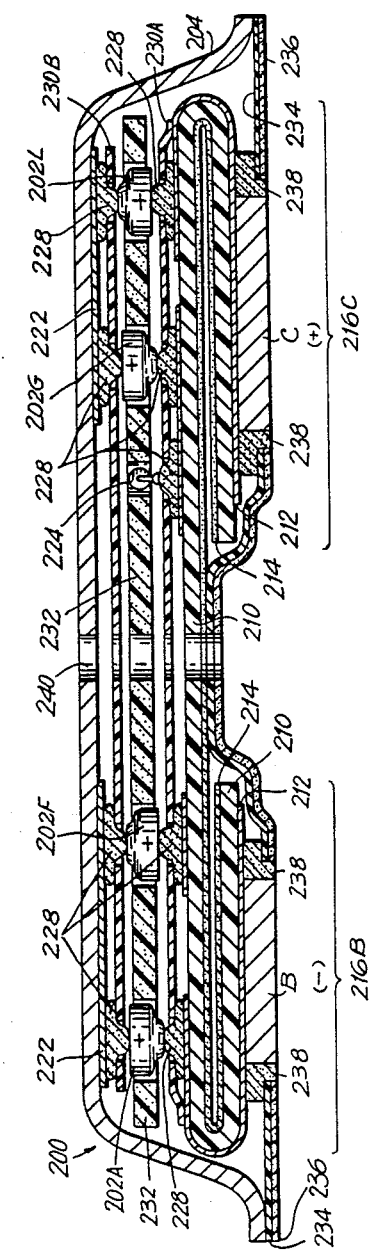
FIG. 12 is a cross-section taken through of line 12—12 of FIG. 11.

Another embodiment of a transdermal drug applicator in accordance with the present invention, which is designated by the numeral 200, is illustrated in FIGS. 11 and 12. Drug applicator 200 includes a pair of optionally replaceable drug reservoirs B and C, and a power source, such as twelve button batteries 202A-L, all enclosed by an outer cover 204, which is preferably aluminized. Button batteries 202A-L are arranged in two units 206 and 208, each including five batteries, namely, batteries 202A-E and 202F-L, respectively. Battery unit 206 is located proximately above reservoir B, which is negative in charge, and battery unit 206 is located proximately above reservoir C, which is positive in charge. Batteries 202A-L can vary in number and voltage in accordance with a particular design for a particular drug or drugs contained in the reservoirs. Each battery illustrated is typically 1.5 volts, but the system can include more or fewer batteries each having a lesser or greater voltage. Alternatively, flat batteries typically approximately 1.5 mm in thickness can be used in lieu of the button batteries. Button batteries 202A-L have vertically opposed terminals. The charges of the topside terminals of button batteries 202A-L are shown in FIG. 1. A flexible plastic substrate 210, such as "Mylar," has electroconductive coating 212, preferably an electroconductive graphite paint, applied to one side and an adhesive layer 214 applied to the opposite side. Substrate 210 is non-conductive, impermeable, stable, and compatible with drugs, adhesives, the skin, and materials from which drug applicator 200 is fabricated. Substrate 210 has end portions 216B and 216C which are each underfolded once in an outward, or downward, direction as viewed in FIG. 10, toward reservoirs B and C so that a topside and a bottomside portion is at each end with conductive paint 212 being in electrical contact with the inner side of reservoirs B and C at end portions 216B and 216C. Conductive paint 212 covers two separate areas of substrate 210 each in contact with end portions 216B and 216C so that there is no direct electrical connection between reservoirs B and C by way of end portions 216B and 216C. Adhesive layer 214 adheres to adhesive layer 214 at the end portions 216B and 216C. Conductive paint 212, which covers the entire undersurface of end portions 216B and 216C of substrate 210, follows the folded contour of substrate 210 inwardly, or upwardly, so that paint 212 is on the top surface side of the main portion of substrate 210 so that paint 212 is in electrical contact with the bottomside terminals of batteries 202A-L. At the areas of battery units 206 facing bottomside terminals 202A-L, paint 212 is configured as printed circuits 218B and 218C, shown in FIG. 11, joining the positive and negative bottomside terminals of the batteries. Printed circuits 220B and 220C, which connect in series the positive and negative topside terminals of batteries 202A-L at battery units 206 and 208, are placed on the underside of a stiff plastic sheet 222, which extends over all batteries 202A-L. A current conditioner 224 is positioned proximate battery unit 208 is connected in series with batteries 202A-L by a printed circuit 226 on the undersurface of plastic sheet 222. Electroconductive adhesive paste drops 228 are preferably used to ensure good electrical connections between the terminals of the batteries and printed circuits 218B and 218C and 220B and 220C. Electroconductive paste drops 228 are also used at the opposed sides of current conditioner 224. An electrical circuit thus exists between reservoirs B and C through the skin upon placement of applicator 200 upon the skin and through batteries 202A-L and current conditioner 224.

A pair of perforated plastic liners 230A and 230B are preferably placed on either side of batteries 202A-L primarily to inhibit any spreading of drops 228. Perforations in liners 230 provide access for drops 228. A spacer, such as foam spacer 232, is preferably positioned between the pair of liners 230A and 230B. A heat sealable plastic liner 234 is positioned on the underside of applicator 200 and is connected to the periphery of cover 204. A skin adhesive 236 is placed on the underside of liner 234. A removable release liner (not shown) is ordinarily placed on the underside of liner 234 and is removed prior to use of the applicator. Sealed edges in the form of sealed side walls 238 are disposed about the periphery of reservoirs B and C in order to prevent passage of the drug or drugs from the reservoirs. The sealed side walls 238 may be formed, if desired, by heat sealing through liner 234 and through the drug reservoir material to substrate 210. Alternately, walls 238 can be formed by using a suitable material such as a silicon adhesive to seal the peripheral reservoir edges and to affix liner 234 to drug reservoirs B and C.

Figure 13:
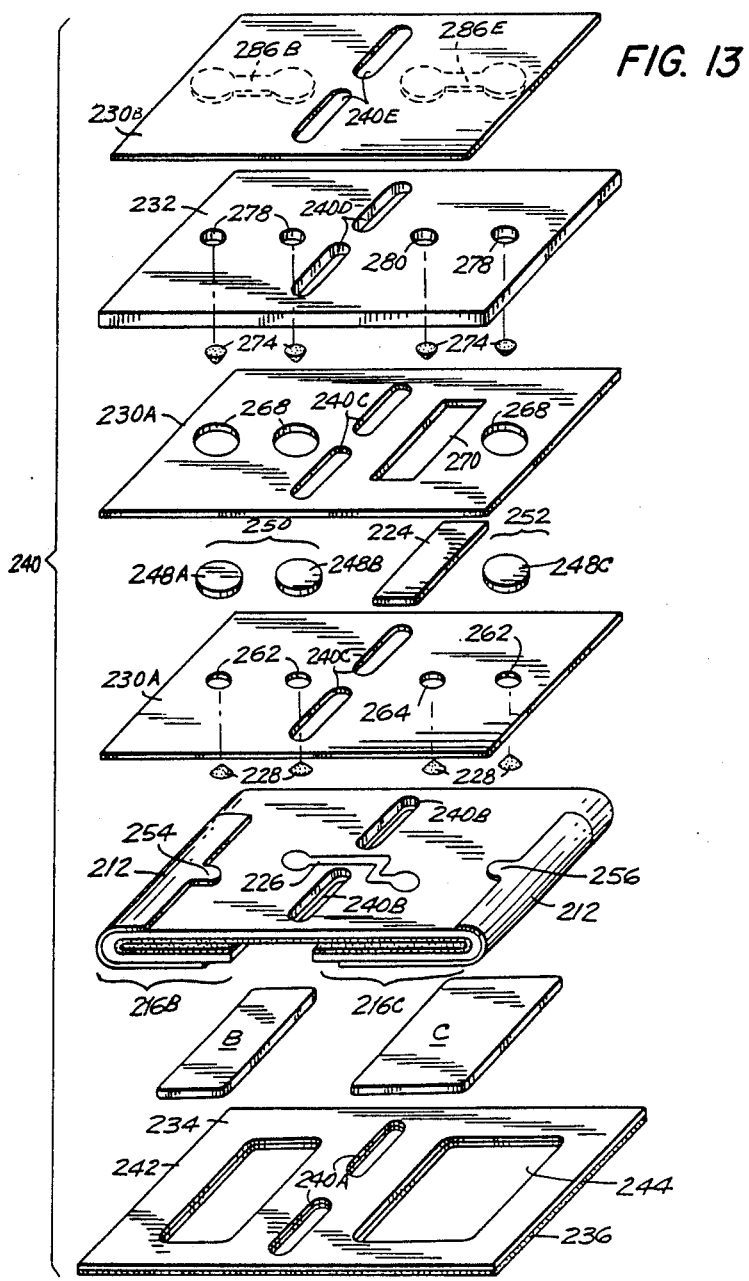
FIG. 13 is an exploded perspective view of the drug applicator shown in FIG. 1 having fewer batteries with the elements shown in their order of assembly.

Drug applicator 200 can be assembled in steps from the components described above. These components are illustrated in FIG. 13 in an exploded perspective view of a drug applicator 242 analogous to drug applicator 200.

The assembly of applicator 242 comprises the following steps:

(a) positioning on a surface the bottom component, which is a heat sealable liner 234 along with a bottommost skin adhesive 236. A pair of reservoir windows 244B and 244C and cutouts 240A that are part of breathing windows 240 are formed in liner 234;

(b) placing drug reservoirs B and C over windows 244B and 244C;

(c) making one downward underfold of each end portion 216B and 216C of substrate 210 so as to make substrate 210 with two layers at each end portion 216B and 216C the lower of which will contact reservoirs B and C. Three button batteries 248A-C are used for drug applicator 242 with batteries 248A and 248B located in battery unit 250 positioned on the left as viewed in FIG. 13 and with battery 248C located in battery unit 252 positioned on the right as viewed in FIG. 13. Conductive paint 212 extends around the bottom sides of 216B and 216C to be in contact with the top sides of reservoirs B and C. Short indentations 254 and 256 of conductive paint 212 extend onto the left and right topside ends, respectively, of substrate 210 where batteries 246A and 246C are to be located. A printed circuit 258 of conductive paint, or ink, of the same material as conductive paint 212 extends between the areas of placement of batteries 248B and 248C in order to connect the terminals of current conditioner 224. A pair of cutouts 240B that are part of breathing windows 240 are formed in the center area of substrate 210;

(d) placing four electroconductive adhesive paste drops 228 on indentations 254 and 256 and on the end portions of printed circuit 258;

(e) placing liner 230A upon substrate 210. Liner 210A has three holes 262 for electroconductive drops 228 for batteries 248A-C and a hole 264 for the electroconductive drop 228 for one end of current conditioner 224 and a pair of cutouts 240C that are a part of breathing windows 240. Nesting holes 262 and 264 are aligned with electroconductive paste drops 228;

(f) placing batteries 248A-C upon liner 230A over nesting holes 262 in electrical contact with drops 228 for batteries 248A and placing current conditioner 224 upon liner 230A upon into electrical contact with drop 228 at the end of printed circuit 226;

(g) placing a spacer, preferably a foam spacer 232, onto liner 230A. Foam spacer 232 forms three nesting holes 268 for receiving batteries 248A-C, a nesting hole 270 for receiving current conditioner 224, and a pair of cutouts 240D that are a part of breathing windows 240. Holes 268 and 270 are placed into nesting alignment with the batteries and current conditioner;

(h) placing electroconductive adhesive paste drops 274 onto the top side terminals of batteries 248A-C; and placing electroconductive adhesive paste drops 274 into electrical contact with the top side terminals of batteries 248A-C; alternatively, in lieu of paste drops 274 an electroconductive paste can be coated on liner 210 and the paste can be die cut with the coating removed before the assembly process so as to isolate electroconductive paste units such as disks, which may be employed in the practice of the invention;

(i) placing a liner 230B over spacer 232. Liner 230B forms three holes 278 for electromagnetic drops 274 for the topside terminals of batteries 248A-C, a hole 280 for the electromagnetic drop 274 for current conditioner 224, and a pair of cutouts 240E that are a part of breathing windows 240;

(j) placing a plastic sheet 222 over liner 230B. Sheet 222 forms a pair of cutouts 240E that are a part of breathing windows 240. All cutouts 240A-240E are positioned in registry to form breathing holes 240. Printed circuits 286B and 286C are located o the underside of plastic sheet 222 connecting the terminals of batteries 248A and 248B and for connecting current conditioner 224 with battery 248C, respectively; and (k) placing a cover 204 (as shown in FIG. 12) over plastic sheet 222 and over the entire assembled applicator 242 and attaching the edges of cover 204 to the topside of heat sealable liner 234.

Flat layered batteries such a batteries 86, 88 illustrated in FIGS. 9 and 10 may be substituted for button batteries 202A-L illustrated in FIGS. 11 and 12 and button batteries 248A-C illustrated in FIG. 13. In such a battery construction, the production method illustrated in FIG. 10 can be used for applicators 200 and 242.

Reservoirs B and C are enclosed at their sides by heat-sealed walls 238. Either one or both reservoirs may be used, that is, a non-drug electrode may be substituted for either reservoir. A pair of breathing windows 240 that extend transversely through the entire drug applicator 242 between battery units 206 and 208 provide a passage for evaporated sweat that may form on the skin.

The two battery units 206 and 208 in FIGS. 11 and 12 and the two battery units 250 and 252 in FIG. 13 may be one battery unit positioned on the side of either drug reservoir B or C;

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. A transdermal drug applicator for application to the skin of a patient which is electrically powered, comprising:

a flexible, non-conductive substrate having conductive coated areas which together form a single flexible member said flexible substrate defining first and second surfaces, and said conductive coated areas being on said first surface and forming drug reservoir electrodes, said flexible member being folded at about 180 degrees at each of two opposite ends to form top side and bottom side portions with the conductive coated areas providing electrical conductors between said top side and said bottom side portions, a plurality of separated drug reservoirs in electrical contact with said drug reservoir electrodes at said bottom side portions, a power source, including an electrical circuit, connected to said conductors at said top side portions for providing current to said plurality of drug reservoirs via said conductors and drug reservoir electrodes, electrical current conditioning means in said circuit with said power source and said drug reservoir electrodes, and a covering for said drug applicator enveloping and enclosing said flexible member, said power source and current conditioning means, and said plurality of drug reservoirs leaving a side of said drug reservoirs free for application.

2. The transdermal drug applicator according to claim 1, wherein said power source is a reusable battery and said cover forms an aperture to receive said reusable power source, said reusable power source having positive and negative terminals adapted to be in electrical contact with said conductive areas so as to form an electrical circuit when said reusable battery is positioned in said aperture.

3. The transdermal drug applicator according to claim 2 further including a programmable control means connected to said reusable power source so as to make a reusable power and control unit adapted to be removably placed in said applicator at said aperture.

4. The transdermal drug applicator according to claim 3, wherein said power source includes a pair of positive and negative sheet electrodes.

5. The transdermal drug applicator according to claim 4, wherein said pair of positive and negative sheet electrodes are zinc and carbon electrodes, respectively.

6. The transdermal drug applicator according to claim 1, wherein said drug reservoirs include gels.

7. The transdermal drug applicator according to claim 6, wherein said gels are reinforced by scrims.

8. The transdermal drug applicator according to claim 2, wherein said drug reservoirs include open cell foam material impregnated with gels.

9. The transdermal drug applicator according to claim 8, further including a semi-permeable membrane in juxtaposition to said drug reservoirs, said semi-permeable membrane having seals so as to define particular drug zones.

10. The transdermal drug applicator according to claim 9, wherein said drug zones contain drugs of different compositions from each other.

11. The transdermal drug applicator according to claim 9, wherein said drug zones contain drugs of different concentrations from each other.

12. The transdermal drug applicator according to claim 1, further including another substrate containing thereon a coated release agent, and said plurality of drug reservoirs being positioned with their free sides in juxtaposition with said release agent of said another substrate.

13. A transdermal drug applicator according to claim 12, wherein said topside portions of said coated areas are joined to terminals of said power source so as to create an electrical circuit when said applicator is applied to the skin.

14. The transdermal drug applicator according to claim 1, wherein some of the conductors are of a predetermined resistance so as to perform the function of a current limiting resistor.

15. The transdermal drug applicator according to claim 1, wherein at least one of said drug reservoir electrodes of one of said plurality of drug reservoirs comprises graphite.

16. The transdermal drug applicator according to claim 15, wherein said plurality of drug reservoirs have opposed inner and outer sides with the outer sides adapted to make contact with the sun of patent upon application, and said at least one electrode mode of graphite is in electrical contact with said inner side of said one drug reservoir.

17. The transdermal drug applicator according to claim 1, further including an adhesive layer on the other side of said non-conductive substrate for firmly securing the folded opposite ends of said non-conductive substrate to itself.

18. The transdermal drug applicator according to claim 1, further including a conductive adhesive at opposite end portions of said conductive coated areas for removably securing said plurality of drug reservoirs to said conductive coated areas.

19. The transdermal drug applicator according to claim 1, further including spacer means having cutouts, and being disposed between said non-conductive substrate and said covering for locating in said cutouts said current conditioning means and said power source.

20. The transdermal drug applicator according to claim 19, including a non-conductive liner having a plurality of perforations juxtaposed on both sides of said spacer means, and said perforations arranged in line with said current conditioning means and said power source.

21. The transdermal drug applicator according to claim 20, including conductive adhesives extending through said perforations for maintaining electrical contact with said current conditioning means and said power source.

22. The transdermal drug applicator according to claim 2, wherein said power source is a plurality of electrically connected batteries.

23. The transdermal drug applicator according to claim 22, wherein said batteries and current conditioning means together with predetermined printed circuit layouts in said applicator and said conductive adhesives form said electrical circuit of the drug applicator.

24. The applicator drug applicator according to claim 23, wherein said predetermined printed circuit layers are formed by a conductive paint.

25. The transdermal drug applicator according to claim 23, wherein said predetermined printed circuit layouts are formed on said liner.

26. The transdermal drug applicator according to claim 20, further including apertures in said spacer means, said liners and said non-conductive substrate forming in registry at least one window in said transdermal drug applicator.

27. The transdermal drug applicator according to claim 1, wherein said electrical circuit includes indicator means in said electrical circuit.

* * * * *